(12) United States Patent
Huang

(10) Patent No.: US 10,478,815 B2
(45) Date of Patent: Nov. 19, 2019

(54) BIOCHIP DEVICE

(71) Applicant: NATIONAL TAIPEI UNIVERSITY OF TECHNOLOGY, Taipei (TW)

(72) Inventor: Jung-Tang Huang, Taipei (TW)

(73) Assignee: NATIONAL TAIPEI UNIVERSITY OF TECHNOLOGY, Taipei (TW)

( * ) Notice: Subject to any disclaimer, the term of this patent is extended or adjusted under 35 U.S.C. 154(b) by 0 days.

(21) Appl. No.: 14/676,602

(22) Filed: Apr. 1, 2015

(65) Prior Publication Data

US 2015/0202626 A1 Jul. 23, 2015

Related U.S. Application Data

(63) Continuation-in-part of application No. 13/671,644, filed on Nov. 8, 2012, now abandoned.

(30) Foreign Application Priority Data

Nov. 8, 2012 (TW) .............................. 100140675 A

(51) Int. Cl.
*A61B 5/157* (2006.01)
*B01L 3/00* (2006.01)
(Continued)

(52) U.S. Cl.
CPC ........ *B01L 3/502715* (2013.01); *A61B 5/157* (2013.01); *A61B 5/150022* (2013.01); *A61B 5/150358* (2013.01); *G01N 27/128* (2013.01); *G01N 33/487* (2013.01); *B01L 2200/027* (2013.01); *B01L 2300/0636* (2013.01); *B01L 2300/16* (2013.01); *B01L 2400/0406* (2013.01); *H01L 2224/04042* (2013.01); *H01L 2224/48227* (2013.01); *H01L 2224/85444* (2013.01);
(Continued)

(58) Field of Classification Search
CPC ......... B01L 3/502715; B01L 2200/027; A61B 5/157; G01N 33/487
See application file for complete search history.

(56) References Cited

U.S. PATENT DOCUMENTS

2005/0042928 A1\* 2/2005 Yi ........................ H01R 12/721
439/637
2007/0231790 A1\* 10/2007 Su ........................ C12Q 1/6825
435/5
(Continued)

FOREIGN PATENT DOCUMENTS

WO WO 2011051405 A1 \* 5/2011 .......... B01L 3/50273

*Primary Examiner* — Paul S Hyun
(74) *Attorney, Agent, or Firm* — WPAT, PC

(57) ABSTRACT

A biochip device for detection of biologic molecules in a fluidic sample is disclosed in this invention. The biochip device comprises a plastic substrate, an IC chip, a sealing cover and a vacuum bag. The plastic substrate comprises a variety of microfluidic structures including an inlet region of loading the fluidic sample, a separation structure, a microfluidic channel, a structure for slowing the flow of the fluidic sample, a reaction region, a detection zone groove, and a closed area for collecting the fluidic sample. The plastic substrate is embedded with an IC chip and covered by a sealing cover made of polydimethylsiloxane, which is encapsulated by a vacuum bag, whereby the microfluidic structures in the plastic substrate are kept in vacuum state inside the vacuum bag.

7 Claims, 8 Drawing Sheets

(51) Int. Cl.
*G01N 27/12* (2006.01)
*G01N 33/487* (2006.01)
*A61B 5/15* (2006.01)

(52) U.S. Cl.
CPC .. *H01L 2924/14* (2013.01); *H01L 2924/1461* (2013.01); *H01L 2924/1579* (2013.01); *H01L 2924/15153* (2013.01); *H01L 2924/16251* (2013.01)

(56) References Cited

U.S. PATENT DOCUMENTS

2010/0181195 A1* 7/2010 Garcia Tello ....... B01F 13/0071
 204/450
2012/0143513 A1* 6/2012 Yang ..................... G01N 21/01
 702/19

* cited by examiner

BIOCHIP DEVICE

CROSS-REFERENCE TO RELATED APPLICATION

This application is a continuation-in-part of U.S. patent application Ser. No. 13/671,644 filed on Nov. 8, 2012, that is incorporated herein by reference in its entirely.

FIELD OF INVENTION

The present invention relates to a biochip device. An IC chip is embedded in a plastic substrate which is formed by way of injection insert molding or hot embossing. The IC chip is used for detecting nanoscale particles or biopolymer in specimen and for electrically transmitting a detecting signal from a fluid sample with high specificity and sensitivity. A PDMS cover plate is bound with the plastic substrate through vacuum packaging to form capillarity or degas statusso as to provide a driving force to drive the fluid sample flowing in the microfluidic channel of the biochip device.

DESCRIPTION OF RELATED ART

A point-of-care diagnosis means a direct measurement at the patient's side with features of disposableness, low cost, simpleness to use. The user uses only a small amount of sample to obtain prompt available test results. Besides the professionals can use point-of-care diagnosis for clinical testing at the hospital, patients or the general public can use the point-of-care diagnosis in any non-hospital places. The device only needs a specimen to be input and the test results are quickly obtained, so with this advantage, the point-of-care is often referred to as one-step assays or one-handling step assays. In the market, the commercially available point-of-care diagnosis is the immunoassay which is a technology commonly used in the detection of antigen. The simplest and commercially available method of point-of-care diagnosis is using the lateral flow assays. Lateral flow assays are low-cost, disposable, and they only need tens of microliters of sample. The most common instance is a pregnancy testing. Its main limitation is a qualitative measurement. However, for many diagnoses quantitative measurement are often needed.

It is well known that the essential feature of the biochip device is disposableness, for example, blood glucose test chip. If the disease detected is complex or it need quantitative measurement, a microfluidic lab-on-chip device needs to employ fluorescence detection analysis. Fluorescence analyzer is a standard equipment of a medical institution. It is expensive, large in volume, and not portable.

Optical methods are often used in biological detection in fluidic samples, for example, a fluorescent analyzer is needed to observe test results, but the fluorescence analyzer is a high cost instrument, it is difficult for the general public to have one in hand. Therefore

SUMMARY

Accordingly, a biochip device is developed by embedding a small detecting IC chip into a microfluidic plastic substrate, the functionality of portable lab-on-chip devices is obtained by connecting to a simple electrical signal reader, such as, a smart mobile device The convenience of the devices are more than that of blood glucose testing. The seamless connection and the smooth flow between the detection area of the IC chip and the microfluidic channel of the plastic substrate is overcome in the present invention. The present invention provides an assembly structure to solve the problem.

The purpose of the present invention is to develop a point-of-care detecting biochip without conducting fluorescence detection in a fluidic sample, by employing an IC chip with function of analysis and amplification of detected signal on an electrical detection platform. The IC chip has the advantages of easiness to be mass-produced, cheapness, small volume, and easiness to detect signal. Therefore in the present invention the detection IC chip is embedded in a plastic substrate, and is covered by a polymer plate to form an innovative biochip.

In one aspect of the invention, a biochip device for detection of biologic molecules in a fluidic sample is provided. The biochip device comprises:

a plastic substrate, having a variety of microfluidic structures including an inlet region for loading the fluidic sample, a separation structure, a microfluidic channel, a structure for slowing the flow of the fluidic sample, a reaction region, a detection zone groove and, a closed area for collecting the fluidic sample, wherein the microfluidic channel is connected from the inlet region, the separation structure, the structure for slowing the flow of the fluidic sample, the reaction region to the closed area for collecting the fluidic sample; and at least one golden fingers located at an edge of the plastic substrate and extended with convergent spacing to the edge of the detection zone groove;

at least one integrated circuit (IC) chip embedded in the detection zone groove of the plastic substrate, the IC chip having at least one detection structure made of a sensing material for generating a detecting signal, and I/O pads for connecting an external power source and outputting the detecting signal, in which the detection structure is modified by using biological conjugates for measuring biologic molecules in the fluidic sample, the I/O pads of the IC chip are wire bonded to the corresponding golden fingers on the edge of the plastic substrate;

a sealing cover made of Polydimethylsiloxane (PDMS) or porous polymer for sealing the plastic substrate embedded with the IC chip, in which a bottom side of the sealing cover corresponding to the detection structure of the IC chip has the microfluidic channel corresponding to the microfluidic channel on the plastic substrate; and a vacuum bag encapsulating the plastic substrate embedded with the IC chip and covered by the sealing cover, wherein to keep the microfluidic structures in the plastic substrate are kept in vacuum state inside the vacuum bag;

wherein the biochip is ready for detection, and when the vacuum bag is unpacked, the fluidic sample loaded at the inlet region flows through the microfluidic channel by degas-driven flow to the detection structure at the IC chip and wherein the volume of the fluidic sample flowing to the closed area for collecting the fluidic sample is fixed and predetermined so as to define a given volume of the fluidic sample to be detected.

According to the invention, the plastic substrate is covered by a PDMS or soft polymer plate to seal the microfluidic structures in the substrate so as to form degas-driven flow of the fluidic sample. The fluidic sample loaded at the inlet region is driven to flow through the microfluidic channel by degas-driven flow to the reaction region, wherein the micro-sized particles in the fluidic sample such as blood cells are indwelled, while the biologic molecules to be detected pass through the microfluidic channel into the detection zone groove, and eventually reach to the closed area for collecting the fluidic sample. The structure for slowing the flow of the fluidic sample can control the flow rate of the fluidic sample to the detection zone groove and the detection structure at the IC chip. The detection structure contains the detection elements by using biological coupling modification specific to biologic molecules in the fluidic sample via sensitive capture for converting into electrical signals. The golden fingers are arranged at the edge of the plastic substrate and used to connect to an USB interface in order to connect to a reader such as a smartphone, to provide power to the IC chip, to read the detecting signal after analog to digital conversion, and finally to display detectable concentration of the fluidic sample on a display of the reader to accomplish the point-of-care diagnosis with high sensitivity and specificity. This biochip device can be mass-produced with cheap price, light-weight and small volume. It is disposable, only needs to use a small amount of sample to promptly detect by using a simple operation. One feature of the invention is that the fluidic sample loaded into the biochip flows through the microfluidic channel by degas-driven flow to the detection structure.

According to the biochip device of the present invention, the sensing material is preferably selected from the group consisting of carbon nanotubes, silicon nanowire, InP nanowire, GaN nanowire, semiconductor nanowire, graphene and nanometer semiconductor film.

According to the biochip device of the present invention, the detection zone groove is preferably based on an electrical sensing mechanism selected from the group consisting of resistor-type, capacitor-type and transistor-type.

According to the present invention, the biological conjugates are preferably selected from the group consisting of antibodies, aptamers, carbohydrates, and combination thereof.

According to the present invention, the fluidic sample is a sample of body fluid selected from the group consisting of blood, cerebrospinal fluid, gastric juice, a variety of digestive juices, semen, saliva, tears, sweat, urine, vaginal fluids, and a solution containing biologic molecules to be detected.

According to the present invention, a top side of the sealing cover is further deposited with a layer of airtight polymer or material, which enhances the reliability of the degas-driven flow.

According to the present invention, the biochip device further comprises a reader for receiving the detecting signal from the biochip, wherein the reader comprises a mobile communication device connected to the biochip device; and a signal processing device connected to the mobile communication device and connected to the golden fingers on the edges of the plastic substrate of the biochip device, wherein the signal processing device comprising a microcontroller (μC), analog-to-digital converter (ADC) and an amplifier, interfaces through a USB with a mobile communication device providing power to the signal processing device and the IC chip, and reading the detecting signal; after analog to digital conversion, a digitized signal is displayed as the concentration of the biologic molecule in the fluid sample as detected in the mobile communication device, to achieve the point-of-care diagnosis.

According to the present invention, the signal processing device preferably comprises a multiplexer, a current amplifier, a microcontroller (μC), power supply (battery), wherein the reader further comprises a wireless communication module, wherein the signals of detection structure on the biochip are scanned and amplified, and transmitted through the wireless communication module to the mobile communications device.

According to the present invention, the inlet region, separation structure, microfluidic channel, the structure for slowing the flow of the fluidic sample, reaction region, detection zone groove and golden fingers are optionally constructed onto the sealing cover.

BRIEF DESCRIPTION OF DRAWINGS

The detailed drawings of this invention will be fully understood from the following descriptions wherein.

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

DETAILED DESCRIPTION

For the convenience of the following description, to define some terms first: A fluid sample is a body fluid, an including blood, a cerebrospinal fluid, a gastric juice, and a variety of digestive juices, a semen, a saliva, tears, sweat, urine, vaginal fluids etc., or a solution containing biologic molecules to be detected. The plastic substrate is a substrate made of polymethylmethacrylate (PMMA), polyethylene terephthalate (PETE), polycarbonate, and Polydimethylsiloxane (PDMS) or a biocompatible polymer material. Nano sensing material can be nanowires (nanowire) used for sensing, which may be selected from the group consisting of carbon nanotubes, silicon nanowire, InP nanowire, GaN nanowire or semiconductor materials, graphene and nanometer semiconductor film, for example, the graphene.

Figure 1:
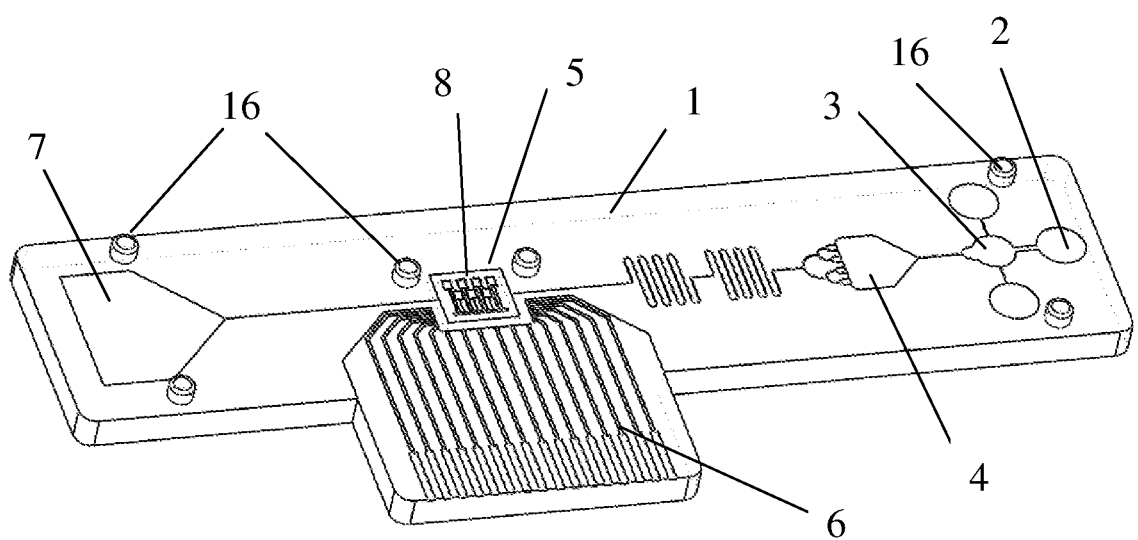
FIG. 1 shows a schematic drawing of the plastic substrate by injection insert molding or by hot embossing of the present invention.

As shown in FIG. 1, the biochip device of the invention comprises a plastic substrate 1, having a variety of microfluidic structures, including at least the inlet region 2 of the fluid sample, a separation structure 3, a reaction region 4, a detection zone groove 5, a closed area for collecting the fluidic sample 7, connected by microfluidic channels. On the plastic substrate, it can achieve separation, reaction and degas-driven purposes. Golden fingers 6 at the edge of the plastic substrate are arranged and extended with convergent spacing to the edge of the detection zone groove 5. The separation structure 3 may be capable to retain blood cells in the cavity and let the fluidic sample pass to the reaction region 4.

At least one integrated circuit (IC) chip 8 is embedded in the detection zone groove 5 of the plastic substrate 1. The IC chip 8 has at least one detection structure, which is modified by using biological conjugates. Each detection structure can measure biologic molecules in the fluidic sample with high specificity and sensitivity. The I/O pads of the IC chip 8 are wire bonded to the corresponding golden fingers 6 or parallel conductor traces on the edge of the plastic substrate detection zone groove 5 to connect to the external power source and to output a detecting signal to the outside.

A sealing cover 14 made of a biocompatible polymer material, such as, Polydimethylsiloxane (PDMS) or porous polymer, is used to seal and to cover the plastic substrate embedded with the IC chip 8. At the bottom side of the sealing cover 14 thereof corresponding to the test structure of the IC chip 8 is a microfluidic channel, which is leakage-freely connected to input/output port of the microfluidic channel on the plastic substrate 1. The fluidic sample in the channel flows by degas-driven flow through the microfluidic channel without leakage. At the top side of the sealing cover, a layer of airtight polymer or material might be deposited to enhance the reliability of the degas-driven flow.

Figure 2:
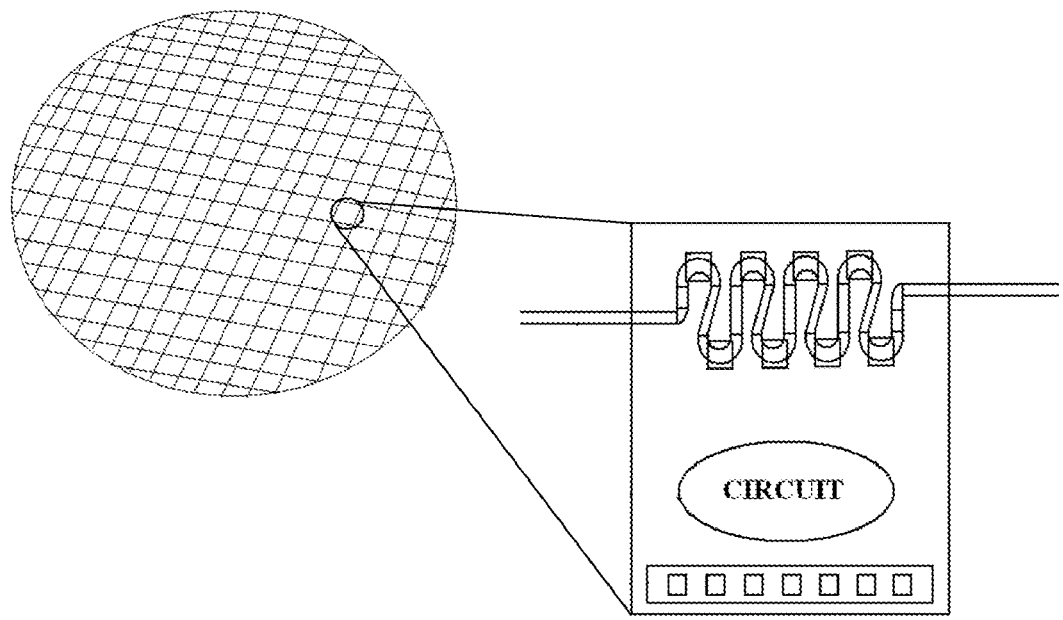
FIG. 2 shows a schematic drawing of IC chip produced by MEMS, CMOS-MEMS, or CMOS NEMS fabrication process in the present invention.

FIG. 2 illustrates the IC chip 8 which contains several biological sensing elements. The sensing mechanism of the sensing elements is selected from resistive, capacitive, or transistors-based sensor. Carbon nanotubes or graphenes or other nano material are working and used as nano sensing material, which are functionalized by specific biopolymers. The biopolymers particularly referred to are antibodies, aptamers, or carbohydrates. The sensing element may be a plurality or array-type ones, to provide the quantitative testing and detection of a variety of target biomarkers of the subject's body. The manufacturing method is divided into two portions, the first portion is to produce an array of carbon nanotube field-effect transistor (CNTFET) or other types of sensors with nano sensing material, while the second portion is using sophisticated dispenser to functionalize nano sensing material with specific biological polymer. The IC chip may further contain the signal processing and amplification circuit fabricated by the use of a CMOS process or a CMOS-MEMS process or a CMOS-NEMS process. IC chip with amplifier may detect very low electrical signal generated by the rare amount of the target polymer, for example 1 pg/ml concentration target polymer correspondingly generates electrical signals only at current level of pA. In case of measured electrical current above nA, the IC chip may not need to include a signal processing and amplification circuit, and could be fabricated by using only the process of micro-electromechanical (MEMS).

Figure 3A:
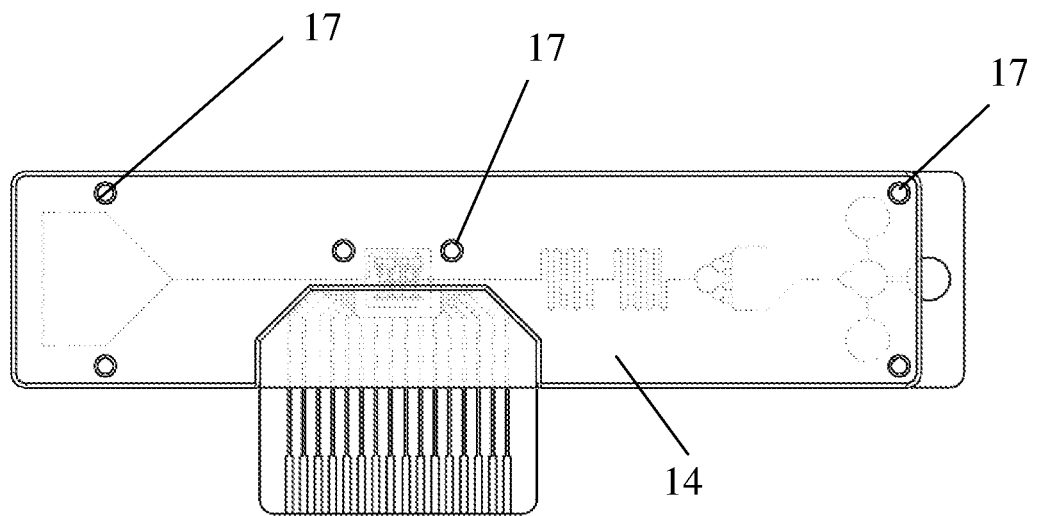
FIG. 3A shows a schematic drawing of the sealing cover for sealing the plastic substrate of the present invention.
Figure 3B:
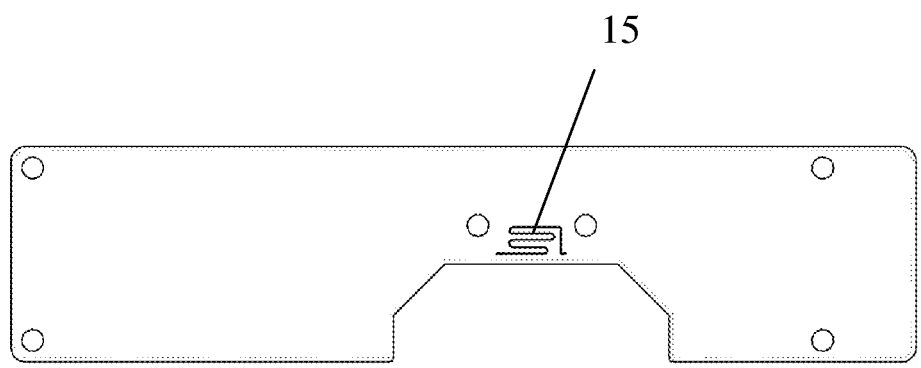
FIG. 3B shows the bottom side of the sealing cover with the microfluidic channel of the present invention.

FIG. 3 shows the sealing cover 14, made of a Polydimethylsiloxane (PDMS) or porous polymer and used to seal the plastic substrate embedded with the IC chip. At the bottom side of the sealing cover 14, an article at the corresponding location to the test structures of the IC chip is a microfluidic channel 15, which is leakage-freely connected to an input/output port of the microfluidic channel on the plastic substrate. The specimen in the tubular microfluidic channel can move by degas-driven flow or capillary flow through test structures at the IC chip without leakage. The sealing cover needs to have open space over pads on the IC chip for wire bonding. The wire bonding is used to connect between golden fingers on the plastic substrate and the IC chip pads. The manufacturing method of the sealing cover 14 is silicone injection molding, or silicone transfer molding technology. Note that after molding, on the top side of the sealing cover, a layer of airtight polymer or material might be deposited to enhance the reliability of the degas-driven flow.

Figure 4A:
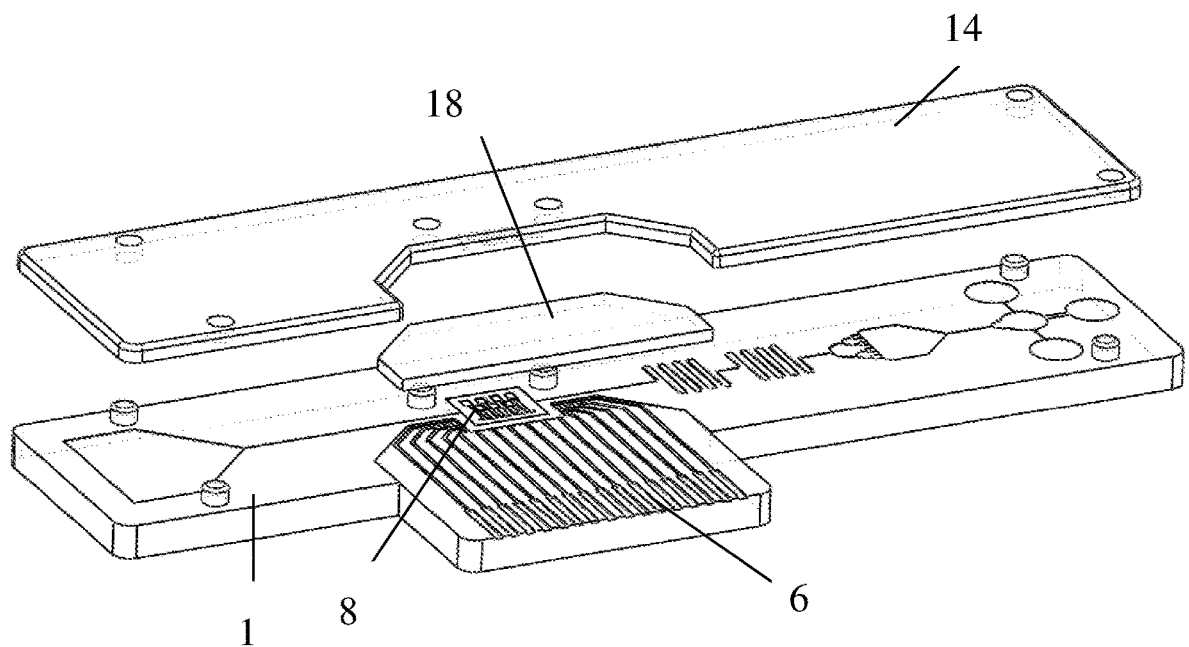
FIG. 4A provides a schematic 3-D view of assembling PDMS cap with the substrate containing microfluidic structures of the present invention.

The assembly procedure of the biochip device in the present invention is described as following:

Step 1, as shown in FIG. 4A, by using vertical injection molding machine, the IC chip is directly placed to the insert mold assembly where the rectangular space is surrounded by four locating pins in the lower mold, by letting the detection area of embedded IC chip be faced downward. The mold cavity formed by the upper mold and the lower mold is the plastic substrate 1. After injection, then cooled, and ejected, it can yield the plastic substrate embedded IC chip containing a variety of microfluidic structures. Note that the IC chip used in this step has already contained nano sensing material deposited on the test structures, e.g. CNTFETs array.

Step 2, as shown in FIG. 4A, to clean the injection-molded microfluidic channel on the plastic substrate and to modify the surface of the overall plastic substrate into hydrophilic condition are demonstrated. The modification methods may be the use of oxygen plasma with Tetraethylorthosilicate (TEOS) immersion. In addition, the PDMS sealing cover 14 is subjected to surface treatment.

Step 3, as shown in FIG. 4A, following surface treatment of embedded IC chip in Step 2 a precision dispenser dispatches and immobilizes the functionalized biopolymer onto nano-sensing materials.

Step 4, to cover and bond the PDMS sealing cover 14 with the plastic substrate 1 by the aid of alignment holes 17 (FIG. 3) on the sealing cover 14 is demonstrated, and the alignment pins 16 (FIG. 1) on the plastic substrate 1 is shown in FIG. 4A. Note that the PDMS sealing cover 14 may fully lay over the microfluidic structures of the plastic substrate 1 to form an enclosed microfluidic space except the inlet.

Figure 4B:
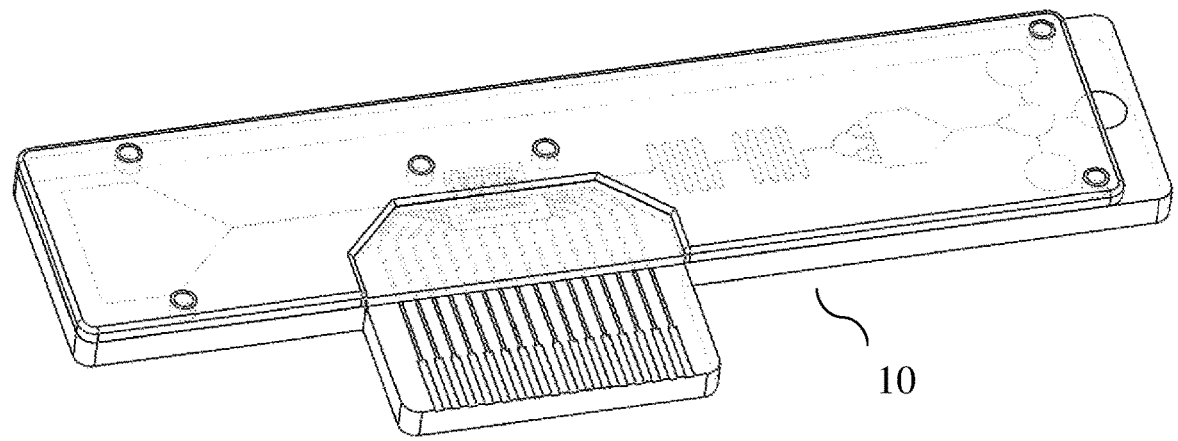
FIG. 4B shows the assembled biochip device of the present invention.

Step 5, the IC chip is wire bonded to the plastic substrate, and then dispensed with glue 18 to protect the bonding wires. The complete assembly of the biochip device 10 is shown in FIG. 4B.

Step 6, the assembled biochip device is loaded into a vacuum bag for further vacuum packaging.

The present invention intends to provide point of care diagnosis for users without expertise of professional medical inspectors. Therefore the volume of each sample offered by the user may not be precise, which may require biochips with automatic quantitative metering ability. Due to the closed outlet of microfluidic channel on the biochip device of the present invention, the volume of the microfluidic structures is fixed, for example, a preferred embodiment is 3-4 microliters (μL). As most people directly puncture finger prick blood roughly 5 microliters, and then drop into the biochip device as the biological sample. Eventually only 3 microliters of blood, for instance, can be precisely metered into detection zone. Even the sample is other body fluids such as urine, as long as it is added dropwise to the inlet of the biochip device more than 3 microliters, 3 microliters would be the basis for calculating accurate concentration, especially for point of care diagnostic biochip devices.

Figure 5:
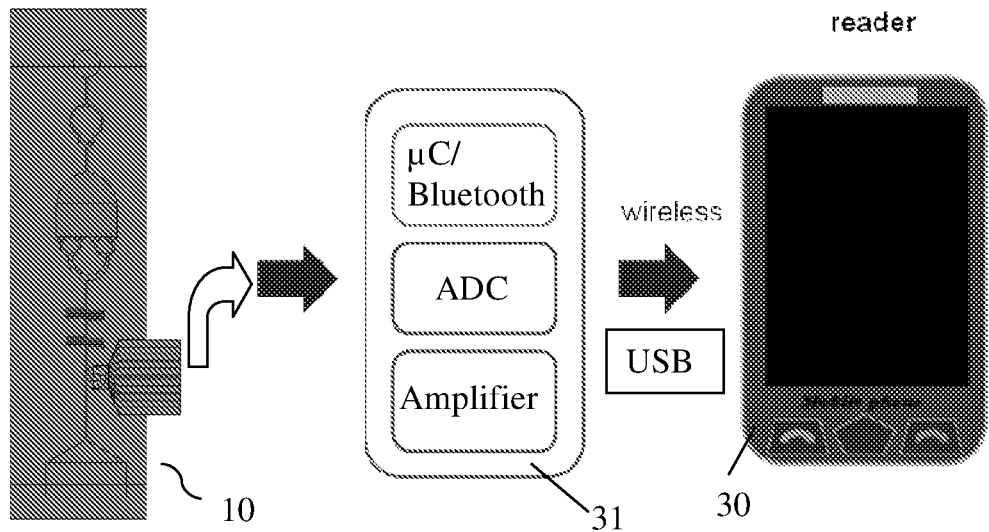
FIG. 5 illustrates a mobile communication device combined with a signal processing device as a reader for displaying the detected signal from the biochip of the present invention.

Referring to FIG. 5, the reader for receiving the detected signal from the biochip device comprises a microcontroller (μC), analog-to-digital converter (ADC), display monitors, and a power supply (battery), such as a notebook computer or mobile phone. Through the USB interface, a connector connected to the golden fingers on the edges of the plastic substrate of the biochip device can provide power to the IC chip and read the detection signal. After analog to digital conversion, the digitized signal could be displayed as the detected concentration in the reader, and achieve the point-of-care diagnosis.

If the IC chip only retains biological sensing without amplification function of signal amplification circuit, the reader for the biochip device 10 could be separated into two parts: one is a mobile communication device 30; the other is a signal processing device 31 connected to the golden fingers set on the edges of the plastic substrate of the biochip device. The signal processing device 31 includes a multiplexer, a current amplifier, a microcontroller (μC), power supply (battery), and optionally a wireless communication module, such as Bluetooth low-power module. The signals of sensing elements on the biochip device 10 are scanned and amplified, and transmitted through the wireless communication module to mobile phone or to other mobile communications device.

The preferred procedure for using the biochip device of the present invention is described below. The user firstly uses a smartphone camera to shoot identification barcode affixed outside of the biochip vacuum packaging or uses a near-field communication (NFC) reader, which may be a standard function of the smartphone, so as to read the attached RFID tags or input identification code on the phone screen through the APP program. Next, the user tears vacuum packaging to remove the present invented biochip, and in 3-5 minutes drops the sample into inlet of the biochip. The specimen is driven under negative pressure flow into the separation structure, the reaction region, the IC chip, the area for collecting the fluidic sample. After waiting about 10 minutes, the user can read the data. The result is corresponding to whether it is positive or negative reaction, as well as its concentration. The data can also be uploaded to the cloud for subsequent processing by the medical staff to do further diagnosis.

Embodiment 1

Figure 6:
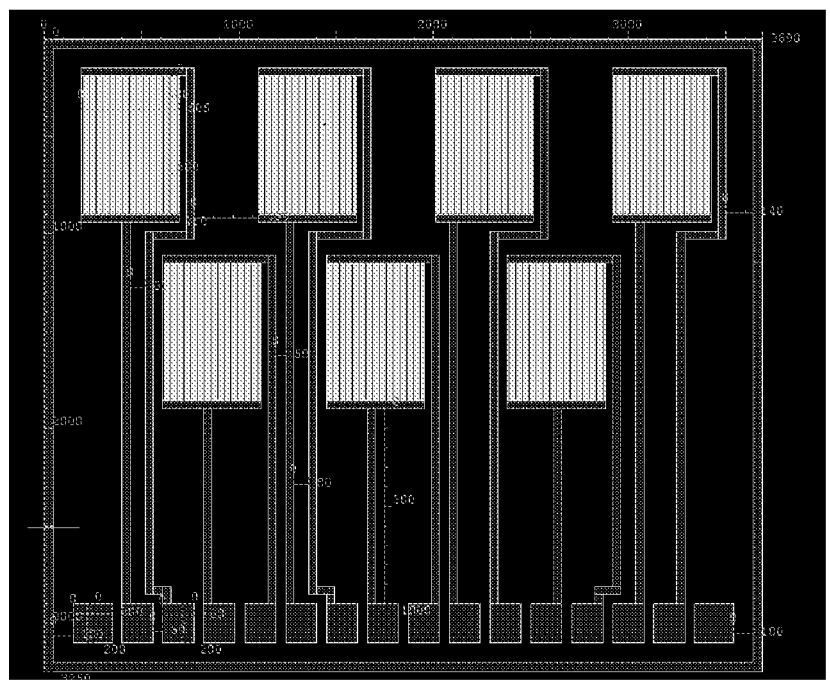
FIG. 6 provides a schematic drawing of the chip of embodiment 1 of the present invention.

FIG. 6 shows an embodiment of the IC chip with chip size of 4*4 (mm$^2$). There is no amplifier or circuit in this IC chip, but main sensing structure composed of seven comb-shaped electrode elements, one of them as the control electrode of the circuit, while the remaining six comb electrode components were given different analytes-specific aptamers modified carbon nanotubes. The target analytes may be six different cancer biomarkers in the serum or the plasma. For wire bonding the pads with I/O ports of the plastic substrate 1, the entire pad layout is at the same side. With the subsequent plastic microfluidic channel packaging, a set of real-time sensing biochip may detect six kinds of different analytes.

Embodiment 2

Figure 7:
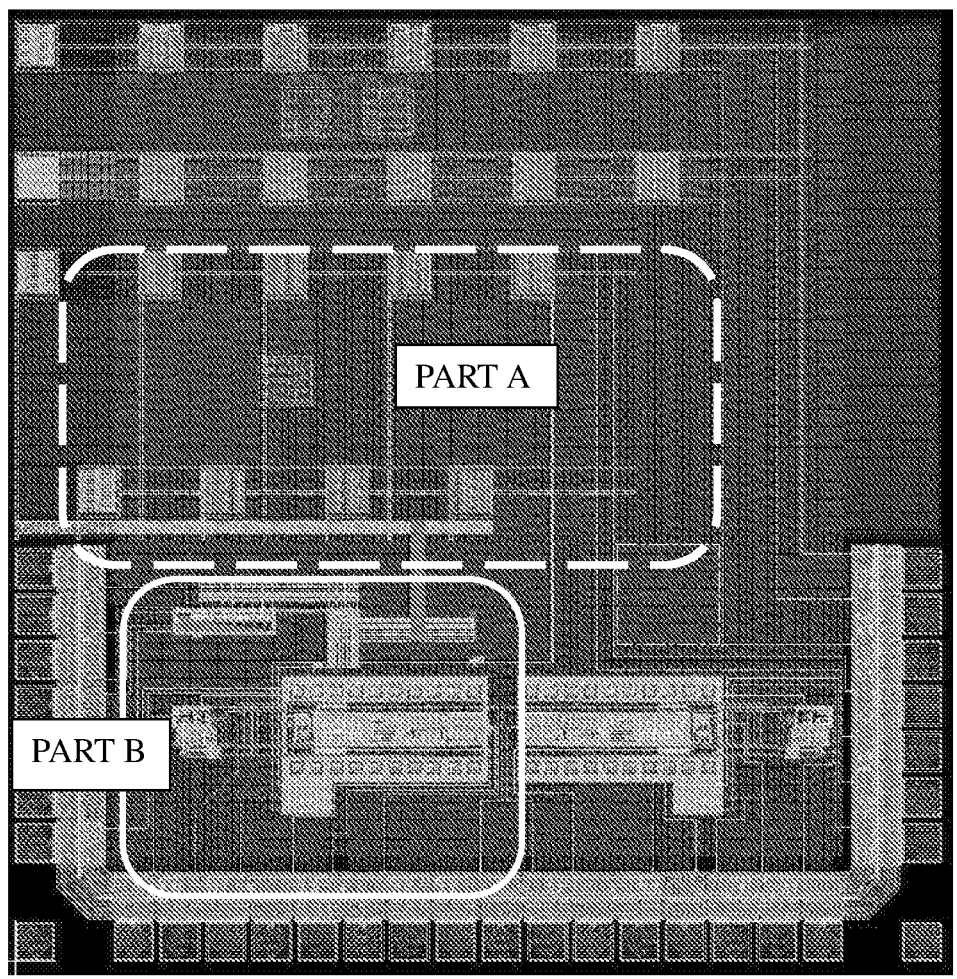
FIG. 7 provides a schematic drawing of the chip of embodiment 2 of the present invention.

FIG. 7 shows another embodiment of the IC chip with chip size of 2.23884*2.28145 (mm$^2$). Part A is a signal processing circuit connected to CNTFETs sensing element through a multiplexer to select different sensing element output. The signal processing circuit mainly comprises a clock generator, a chopper, and switched capacitor circuit. Part B is the sensing structure composing of nine comb-shaped electrode elements, one of them as the control electrode of the circuit, while the remaining eight comb-electrode components were given different analyte-specific aptamers modified carbon nanotubes. For wire bonding the pads with I/O ports of the plastic substrate 1, the entire pad layout is on the same side. With the subsequent plastic microfluidic channel packaging, a set of real-time sensing biochip may detect eight kinds of different analytes.

Embodiment 3

Figure 8:
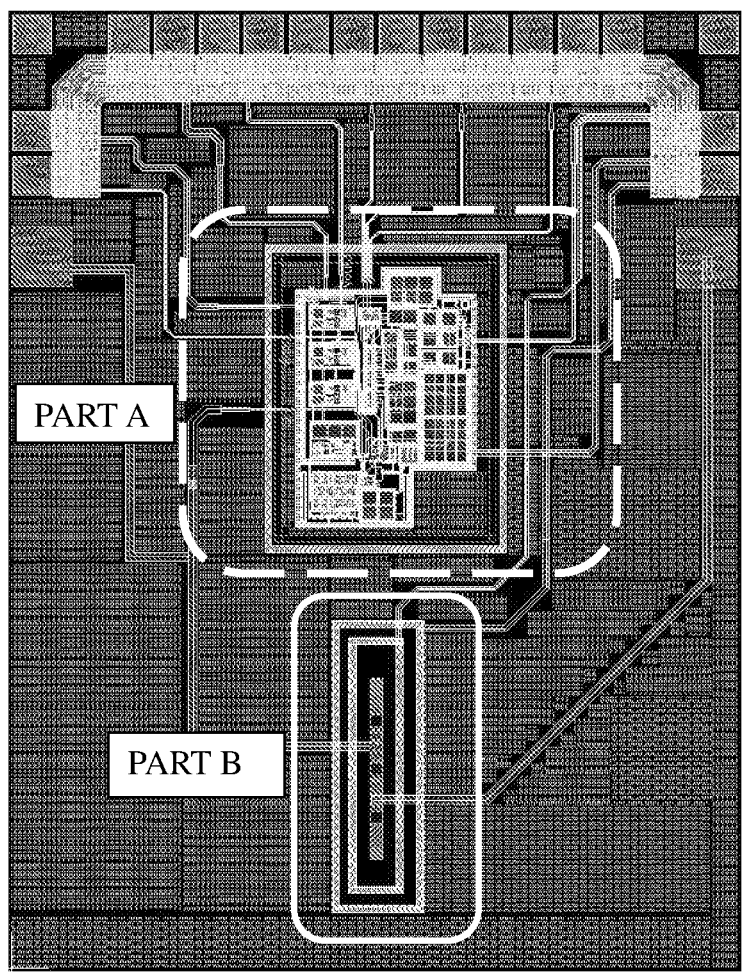
FIG. 8 provides a schematic drawing of the chip of embodiment 3 of the present invention.
Figure 9:
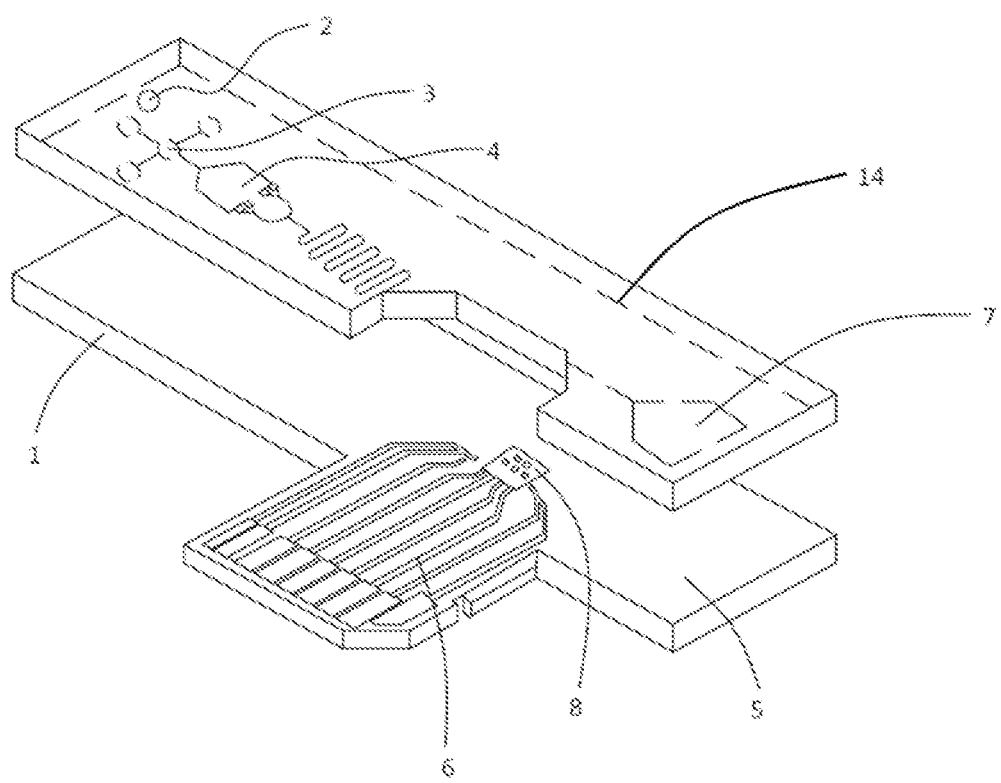
FIG. 9 provides a schematic drawing of the chip of another embodiment of the present invention, which comprises a plastic substrate 1 having golden fingers 6 and a detection zone groove 5, in which at least one IC chip 8 is embedded; and a sealing cover 14, onto which there are an inlet region 2, a separation structure 3, a reaction region 4, and a closed area for collecting the fluidic sample 7, connected by microfluidic channels.

FIG. 8 illustrates another embodiment of the IC chip with chip size of 2.364*1.794 (mm$^2$). Part A shows the amplifier circuit capable of measuring nA to μA current changes, which mainly use the charge integrator for amplifying the input current signal into a voltage output. This area also contains three sets of operational amplifiers, switches, oscillators, and a multiplexer. The entire pads are at the same side, in order to facilitate follow-up integration with the plastic substrate 1. Part B is the counting structural elements, having a pore with the size of 30 microns, for counting the number of cancer cells in size of 15 to 25 microns. Since the height of the pore and microfluidic channel is around 30 microns, it needs an electroforming process to fabricate the thick metal seeding from the PAD layer of the IC chip.

In this embodiment, the PDMS plate would not cover the outlet of microfluidic channel, but let micro fluid flow through the outlet and fully count all the cancer cells in the sample.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention.

What is claimed is:

1. A biochip device for detection of biologic molecules in a fluidic sample, comprising:
   (1) a plastic substrate, having a variety of microfluidic structures including a detection zone groove, and a closed area for collecting the fluidic sample, wherein a plurality of golden fingers are located at an edge of the plastic substrate and extended with convergent spacing to an edge of the detection zone groove;
   (2) at least one integrated circuit (IC) chip embedded in the detection zone groove of the plastic substrate, the IC chip having at least one detection structure made of a sensing material for generating a detecting signal, and I/O pads for connecting an external power source and outputting the detecting signal, in which the at least one detection structure is a modified structure modified by using biological conjugates for measuring biologic molecules in the fluidic sample, the I/O pads of the IC chip are wire bonded to the plurality of golden fingers on the edge of the plastic substrate;
   (3) a sealing cover made of Polydimethylsiloxane (PDMS) for sealing the plastic substrate embedded with the IC chip, being disposed on the plastic substrate with its bottom side facing the substrate, wherein there are an inlet region for loading the fluidic sample, a separation structure, microfluidic channels, a structure for slowing the flow of the fluidic sample, and a reaction region on the sealing cover; and wherein there is lateral space formed between the detection zone groove and the closed area for collecting the fluidic sample, and the lateral space spans between the plastic substrate and the bottom side of the sealing cover; and wherein the microfluidic channels are connected from the inlet region, the separation structure for slowing the flow of the fluidic sample, the reaction region to the closed area for collecting the fluidic sample; and (4) a vacuum bag encapsulating the plastic substrate embedded with the IC chip and covered by the sealing cover, whereby the microfluidic structures in the plastic substrate are kept in vacuum state inside the vacuum bag;

wherein the biochip device is ready for detection, and when the vacuum bag is unpacked, the fluidic sample loaded at the inlet region flows through the microfluidic channels by degas-driven flow and to the at least one detection structure at the IC chip and wherein the volume of the fluidic sample flowing to the closed area for collecting the fluidic sample is fixed and predetermined so as to define a given volume of the fluidic sample to be detected.

2. The biochip device according claim 1, wherein the sensing material is selected from the group consisting of carbon nanotubes, silicon nanowire, InP nanowire, GaN nanowire, semiconductor nanowire and nanometer semiconductor film.

3. The biochip device according claim 1, wherein the at least one detection structure is based on an electrical sensing mechanism selected from the group consisting of resistor-type, capacitor-type and transistor-type.

4. The biochip device according claim 1, wherein the biological conjugates are selected from the group consisting of antibodies, aptamers, carbohydrates, and combination thereof.

5. The biochip device according claim 1, wherein the fluidic sample is a sample of body fluid selected from the group consisting of blood, cerebrospinal fluid, gastric juice, a variety of digestive juices, semen, saliva, tears, sweat, urine, vaginal fluids, and a solution containing biologic molecules to be detected.

6. The biochip device according claim 1, wherein a top side of the sealing cover is further deposited with a layer of airtight polymer or material, which enhances the reliability of the degas-driven flow.

7. The biochip device according claim 1, further comprising a reader for receiving the detected signal from the biochip, wherein the reader comprises a mobile communication device and a signal processing device; the mobile communication device is connected to the biochip device; the signal processing device is connected to the mobile communication device and is also connected to the plurality of golden fingers on the edges of the plastic substrate of the biochip; the signal processing device comprises a microcontroller (μC), an analog-to-digital converter (ADC) and an amplifier; wherein the reader further comprises an interface connected to the mobile communication device and providing power to the signal processing device and the IC chip; the interface comprises a connecter configured to read the detecting signal.

* * * * *